United States Patent [19]
Redding et al.

[11] Patent Number: 5,460,061
[45] Date of Patent: Oct. 24, 1995

[54] ADJUSTABLE CONTROL PEDAL APPARATUS

[75] Inventors: Harry L. Redding, North Port, Fla.; Christopher Bortolon, Clawson, Mich.

[73] Assignee: Comfort Pedals, Inc., Warren, Mich.

[21] Appl. No.: 123,336

[22] Filed: Sep. 17, 1993

[51] Int. Cl.$^6$ ........................................ G05G 1/14
[52] U.S. Cl. ................. 74/512; 74/513; 74/560
[58] Field of Search ................. 74/512, 513, 560; 180/334, 326

[56] References Cited

U.S. PATENT DOCUMENTS

| | | | |
|---|---|---|---|
| 1,425,413 | 8/1922 | Pag" | 74/560 |
| 1,454,258 | 5/1923 | Adams | 74/513 |
| 1,929,409 | 10/1933 | Carr . | |
| 2,468,977 | 5/1949 | Hobbs | 74/512 |
| 2,860,720 | 11/1958 | Huff et al. . | |
| 2,906,842 | 9/1959 | Brin . | |
| 2,908,183 | 10/1959 | DiGiovanni . | |
| 2,936,867 | 5/1960 | Perry . | |
| 3,151,499 | 10/1964 | Roe | 74/560 |
| 3,282,125 | 11/1966 | Dully . | |
| 3,301,088 | 1/1967 | White | 74/560 |
| 3,319,487 | 5/1967 | Lystad et al. . | |
| 3,338,348 | 8/1967 | Roethlisberger et al. . | |
| 3,511,109 | 5/1970 | Tanaka | 74/560 |
| 3,563,111 | 2/1971 | Zeigler | 74/512 |
| 3,643,524 | 2/1972 | Herring | 74/512 |
| 3,643,525 | 2/1972 | Gibas | 74/512 |
| 3,691,868 | 9/1972 | Smith | 74/512 |
| 3,754,480 | 8/1973 | Bodnar et al. | 74/512 |
| 3,765,264 | 10/1973 | Bruhn, Jr. | 74/512 |
| 3,828,625 | 8/1974 | Bruhn, Jr. | 74/512 |
| 3,943,795 | 3/1976 | Kenney | 74/562.5 |
| 3,975,972 | 8/1976 | Muhleck | 74/560 |
| 4,497,399 | 2/1985 | Kopich | 192/111 |
| 4,875,385 | 10/1989 | Sitrin | 74/512 |
| 4,989,474 | 2/1991 | Cicotte et al. | 74/512 |
| 5,010,782 | 4/1991 | Asano et al. | 74/512 |
| 5,078,024 | 1/1992 | Cicotte et al. | 74/512 |
| 5,351,573 | 10/1994 | Cicotte | 74/512 |

FOREIGN PATENT DOCUMENTS

| | | | |
|---|---|---|---|
| 2293342 | 7/1976 | France . | |
| 2132753 | 1/1973 | Germany | 74/560 |
| 2644628 | 12/1977 | Germany | 74/560 |
| 585220 | 4/1993 | Japan | 74/512 |
| 920784 | 8/1961 | United Kingdom | 74/512 |
| 952831 | 3/1964 | United Kingdom . | |

*Primary Examiner*—Charles A. Marmor
*Assistant Examiner*—Nathan O. Jensen
*Attorney, Agent, or Firm*—Young, MacFarlane & Wood

[57] ABSTRACT

An adjustable control pedal apparatus for a motor vehicle including an accelerator control pedal assembly and a brake control pedal assembly. A motor is positioned between the control pedal assemblies and includes a motor drive shaft driving first and second cables secured to the opposite ends of the drive shaft. The cables extend respectively to the brake and accelerator pedal assemblies so as to provide rotary cable movement at each pedal assembly. A transmission at each pedal assembly converts the rotary cable movement to rotary movement of a screw member which slidably adjusts a pedal arm along an adjuster member. As the pedal arm moves along the adjuster member, the pivot axis of the assembly is moved so as to maintain a substantially constant feel for the pedal irrespective of the adjusted position of the pedal arm. The pivot axis is moved by a cam pin driven by the pedal arm and received in a slot in a cam member carrying the pivot axis pin. A slack takeup device is provided at the intersection of the pedal arm and the adjuster member to preclude angular movement between the pedal arm and the adjuster member while not interfering with the sliding movement of the pedal arm along the adjuster member. A cover of inverted U configuration fits over the adjuster member to protect the sliding interface between the pedal arm and the adjuster member and is fixedly secured to outboard faces of the adjuster member to rigidify the adjuster member.

10 Claims, 6 Drawing Sheets

ADJUSTABLE CONTROL PEDAL APPARATUS

BACKGROUND OF THE INVENTION

This invention relates to control pedal apparatuses and more particularly to adjustment means for selectively adjusting the position of one or more of the control pedals of a motor vehicle.

In a conventional automotive vehicle, pedals are provided for controlling brakes and engine throttle. If the vehicle has a manual transmission, a clutch pedal is also provided. These pedals are foot operated by the driver. In order for the driver to obtain the most advantageous position for working these controls, the vehicle front seat is usually slidably mounted on a seat track with means for securing the seat along the track and a plurality of adjustment positions.

The adjustment provided by moving the seat along the seat track does not accommodate all vehicle operators due to differences in anatomical dimensions. Further, there is growing concern that the use of seat tracks, and especially long seat tracks, constitutes a safety hazard and that the seat may pull loose from the track during an accident with resultant injuries to the driver and/or passengers. It is therefore desirable to either eliminate the seat track entirely or shorten the seat track so that it will be strong enough to retain the seat during an impact. Shortening or eliminating the seat track requires that means be provided to selectively move the various control pedals to accommodate various sized drivers.

Various proposals were made over a period of many years to provide selective adjustment of the pedal positions to accommodate various sized drivers, but none of these proposals met with any significant commercial acceptance since the proposed mechanisms were unduly complex and expensive and/or were extremely difficult to operate and/or accomplish the required pedal adjustment only at the expense of altering other critical dimensional relationships as between the driver and the various pedals. Recently, a control pedal mechanism has been developed which is simple and inexpensive, easy to operate, and that accomplishes the required pedal adjustment without altering other critical dimensional relationships as between the driver and the various pedals. This control pedal mechanism is disclosed in U.S. Pat. Nos. 4,875,385, 4,989,474, and 5,078, 024, all assigned to the assignee of the present application. The present invention represents improvements to the basic adjustable control pedal design disclosed in these patents.

SUMMARY OF THE INVENTION

This invention is directed to the provision of a simple and inexpensive control pedal mechanism in which the pedal position is readily adjusted without disturbing the essential dimensional relationships in the control environment.

The invention control pedal apparatus includes an adjuster member mounted for movement relative to the motor vehicle structure, a pedal arm mounted for sliding movement along the adjuster member, means operative to move the pedal arm slidably along the adjuster member, and means operative in response to movement of the pedal arm along the adjuster member to move the pivot axis of the control pedal apparatus.

According to an important feature of the invention, the adjuster member and pedal arm include coacting mounting portions which define an intersection and the apparatus includes a slack takeup assembly positioned at the intersection and operative to preclude relative angular movement between the adjuster member and pedal arm at the intersection. This arrangement eliminates undesired relative movement as between the pedal arm and the adjuster member, whereby to provide a solid pedal feel for the driver and eliminate rattle in the control pedal apparatus, while not interfering with the smooth sliding movement of the pedal arm along the adjuster member.

In one embodiment of the invention, the slack takeup assembly includes a bracket secured to the pedal arm proximate the intersection between the pedal arm and the adjuster member, a block positioned on the bracket, and a plurality of plug members mounted in the block and extending beyond the block to engage a face of the adjuster member.

In another embodiment of the invention, the slack takeup assembly includes a lever member pivotally mounted on the pedal arm proximate the intersection and adjuster means operative to move a toe portion of the lever member upwardly into contact with a face of the adjuster member to take up slack between the members.

According to a further feature of the invention, the means for moving the pivot axis of the pedal assembly in response to sliding movement of the pedal arm on the adjuster member comprises a cam member, a pivot axis pin mounted on the cam member and defining the pivot axis of the pedal assembly, and a link connected at one end to the pedal arm and cammingly coacting at its other end with the cam member. This arrangement provides a ready and efficient means to selectively move the cam member and thereby the pivot axis even in the cramped environment which is typical of the area beneath the instrument panel of a motor vehicle.

According to a further feature of the invention, the cam member is pivotally mounted on the adjuster member, the one end of the link is pivotally mounted on the pedal arm and the other end of the link is received in a slot in the cam member, and the pivot axis pin is received in a slot in the adjuster member. This specific arrangement provides precise and positive movement of the pivot axis of the pedal assembly in response to adjusting movement of the pedal arm on the adjuster member.

According to a further feature of the invention, the means for moving the pivot axis of the pedal assembly in response to adjusting movement of the pedal arm along the adjuster member includes a cam member pivoted on the adjuster member and including a slot and a pivot axis pin defining the pivot axis of the pedal assembly, and a cam pin received in the slot and operative in response to sliding movement of the pedal apparatus on the adjuster member to pivot the cam member on the adjuster member and adjust the position of the pivot axis pin and thereby of the pivot axis of the pedal assembly. In one embodiment of the invention, the cam pin is mounted on the pedal arm and, in another embodiment of the invention, the apparatus further includes a link pivotally mounted at one end on the pedal arm and the cam pin is mounted on the other end of the link.

According to a further feature of the invention, the pedal assembly includes first and second control pedal assemblies each including a screw member and a pedal arm mounted for adjusting movement in response to rotation of the screw member to adjust the position of the pedal arm relative to the vehicle structure, and the apparatus includes a motor positioned on the motor vehicle structure between the first and second pedal assemblies and including a motor drive shaft, first and second cables secured to the opposite ends of the drive shaft and extending respectively to the first and second pedal assemblies so as to provide rotary cable movement at each pedal assembly in response to actuation of the motor, and means at each pedal assembly operative to convert the rotary cable movement to rotary movement of the screw member. This arrangement allows a single motor positioned between the two pedal assemblies to positively and precisely position the two pedal assemblies in response to actuation of the motor.

BRIEF DESCRIPTION OF THE DRAWING

FIG. 2 is a somewhat schematic view of the brake control pedal assembly;

FIG. 3 is a cross-sectional view taken on line 3—3 of FIG. 2;

FIGS. 12–17 are detailed views of a bushing assembly for use with the invention control pedal apparatus; and

DETAILED DESCRIPTION OF THE PREFERRED EMBODIMENTS

The invention control pedal apparatus, broadly considered, includes a brake pedal assembly 10 and an accelerator pedal assembly 12. It will be understood that the pedal assemblies 10 and 12 are mounted side by side in conventional fashion on the dash panel 14 of the associated motor vehicle and are simultaneously adjusted to move the respective pedal pads of the pedal assemblies toward or away from the driver to selectively accommodate various driver statures.

Brake pedal assembly 10 (FIGS. 1 and 2) includes a bracket 16, an adjuster member 18, a pedal arm 20, a cam member 22, and a link 24. All of the members, unless otherwise indicated, are formed of a suitable ferrous material.

Figure 1:
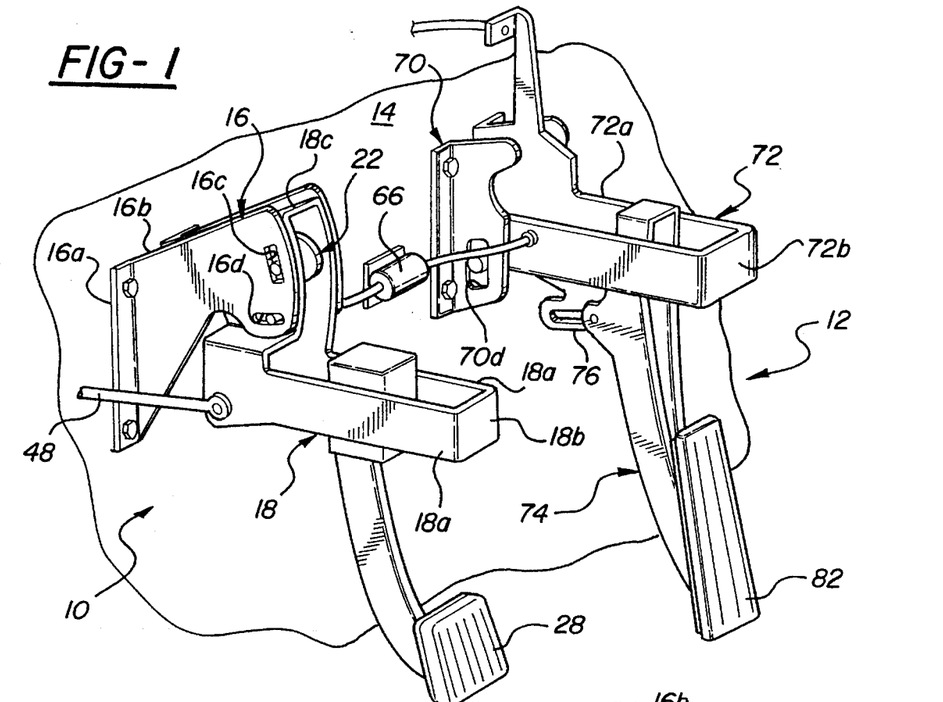
FIG. 1 is a fragmentary perspective view of a control pedal apparatus according to the invention and including, a brake control pedal assembly mounted side by side to an accelerator control pedal assembly.
Figures 2, 13:
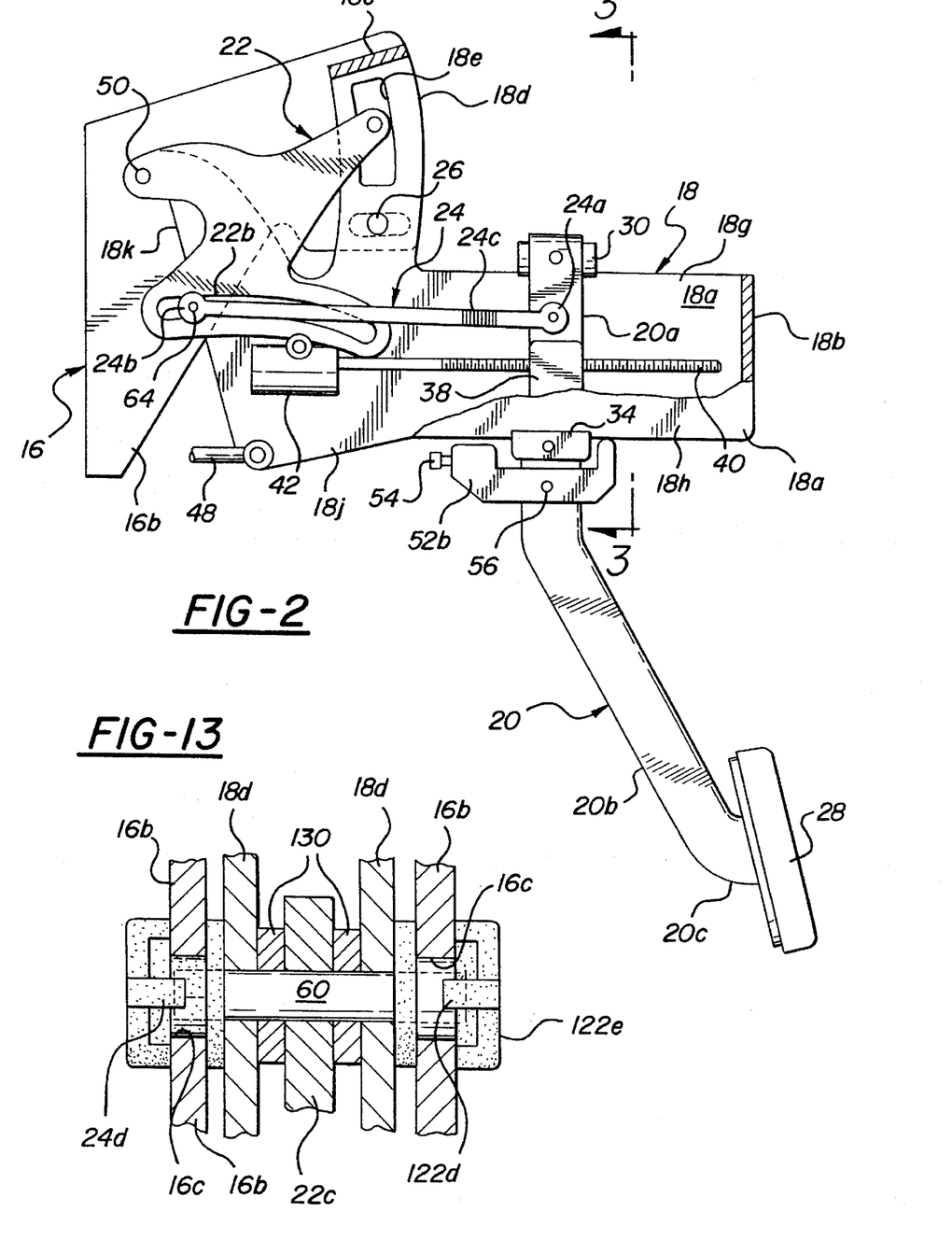

Bracket 16 includes a base portion 16a adapted to be fixedly secured to the dash panel of the vehicle and a pair of spaced side plate portions 16b extending rearwardly from the base portion. Each side plate portion 16b includes an arcuate generally vertically extending slot 16c and an arcuate generally horizontally extending slot 16d positioned below slot 16c.

Adjuster member 18 includes a pair of spaced side plate portions 18a joined by a rear end wall 18b and an upper end wall 18c. A pin 26 secured to an upstanding portion 18d of each side plate portion 18a guides slidably in a respective arcuate slot 16d in a respective bracket side plate portion 16b. An arcuate slot 18e, corresponding in size and configuration and generally aligned with the corresponding slot 16d in a respective bracket side plate portion 16b, is provided in each upstanding portion 18d. One of the side plate portions 18a of the adjuster member is cranked inwardly at 18f (FIG. 3) so as to enable the forward portions of the side plate portion of the adjuster member to be positioned between the spaced bracket side plate portions 16b while enabling the rearward portion of the adjuster member to assume a more widely spaced configuration to accommodate the pedal arm 20 and associated drive and guide structures. A brake actuation rod 48 is pivotally secured to a forward end portion 18j of one of the adjuster member side plate portions and each adjuster member side plate portion further includes an upwardly and forwardly extending portion 18k.

Pedal arm 20 includes an upper portion 20a positioned between the spaced side plates 18a of the adjuster member and a lower portion 20b defining a lower end 20c mounting the brake pedal 28. The upper portion 20a of pedal arm 20 is mounted for adjustable sliding movement along the adjuster member by a pair of upper guide shoes or blocks 30 (FIG. 3) pivotally mounted on a pin 32 passing through the pedal arm and a pair of lower guide shoes or blocks 34 pivotally mounted on a pin 36 passing through the pedal arm. Each upper guide shoe 30 includes a downwardly opening groove 30a slidably embracing the upper edge 18g of a respective adjuster member side plate portion 18a and each lower shoe 34 includes an upwardly opening groove 34a slidably engaging the lower edge 18h of a respective adjuster member side plate portion 18a. Upper shoes 30 and lower shoes 34 will be seen to coact to allow the pedal arm to be moved slidably fore and aft along the side plate portions 18a of the adjuster member so as to selectively move the brake pedal 28 fore and aft with respect to the driver.

A plastic generally rectangular nut 38 (FIG. 3) is secured to the side face of pedal arm upper portion 20a between pins 32 and 36 and includes a threaded central axial bore 38a threadably receiving a screw member 40 comprising the output shaft of a transmission mechanism 42 (FIGS. 2 and 4) secured as by a fastener 44 to one of the side plate portions 18a of the adjuster member and including a cable inlet socket 42a receiving a drive cable 46 passing through a cut-out 18i in the other side plate portion 18a of the adjuster member. Transmission member 42 may, for example, comprise a unit available from Hancock Division of ITT Automotive of Auburn Hills, Mich. as Part No. 2-81219-X1.

A slack adjuster assembly is provided at the intersection of upper pedal arm portion 20a and adjuster member side plate portions 18a to preclude unwanted and inadvertent angular movement between the pedal arm and the adjuster member. The slack takeup assembly (FIGS. 4 and 5) includes a lever 52 and an adjuster screw 54. Lever 52 is mounted in straddling relation to the upper end 20a of the pedal arm with the pedal,arm passing through an aperture 52a in the lever. Lever 52 further defines a forward upstanding portion 52b threadably receiving screw 54 and a pair of forward toe portions 52c spaced apart a distance corresponding to the spacing of the side plate portions 18a of the adjuster member. Lever 52 is pivotally mounted on the upper pedal arm portion 20a by a pivot pin 56 passing through the pedal arm. The opening 52a in the lever is positioned such that the toe portions 52c of the lever respectively engage the lower side edges 18h of the adjuster member side plate portion 18a. Following the assembly of the pedal arm to the adjuster member utilizing the guide blocks 30 and 34, adjuster screw 54 is selectably adjusted to bring toe portions 52b into engagement with the lower edges 18h of the side plate portions 18a of the adjuster member so as to take up any slack in the sliding assembly of the pedal arm on the adjuster member and preclude relative angular movement of the pedal arm relative to the adjuster member, thereby eliminating any annoying wobble of the pedal arm relative to the adjuster member and any resultant rattling noises.

Cam member 22 (FIGS. 2 and 4) includes an upwardly extending forward portion 22a positioned between adjuster member portions 18k and pivotally mounted on a pin 50 extending between the upper ends of adjuster member side plate portions 18k; a lower arcuate slot 22b; and an upwardly extending rearward portion 22c mounting a pivot axis pin 60 (FIG. 3) including portions 60a extending laterally from each side face of the cam member. Each pin portion 60a is positioned in arcuate slots 18e and 16c of a respective adjuster member portion 18d and bracket portion 16b.

Figure 4:
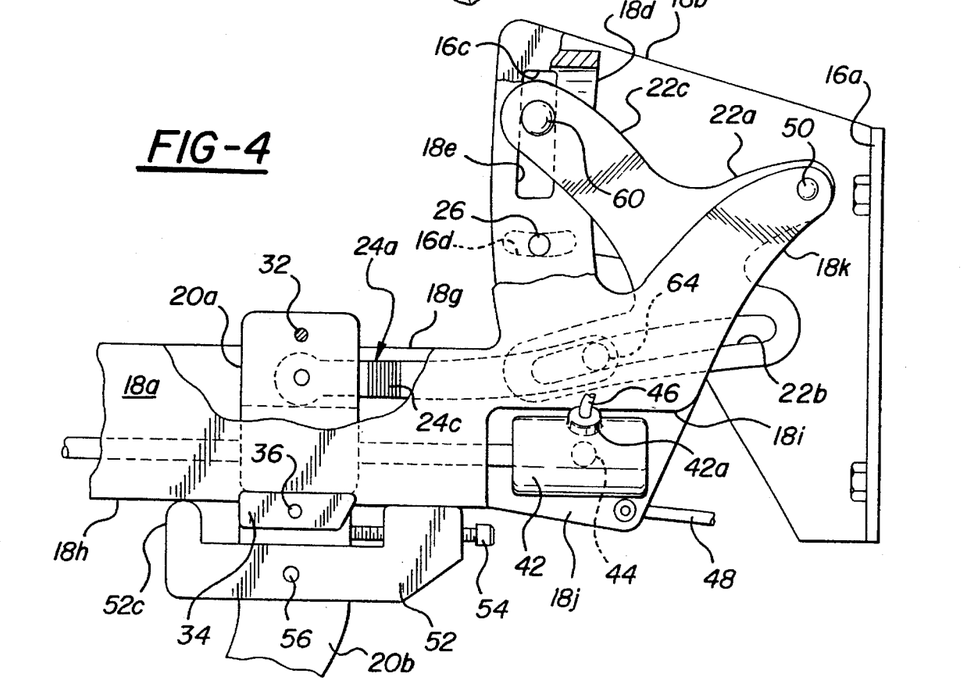
FIG. 4 is a fragmentary view of the brake control pedal assembly.

Link 24 is pivotally mounted at its rearward end 24a to the upper portion 20a of the pedal arm above nut 38 as, for example, by a pin 62 and includes a cam pin 64 mounted on its forward end 24b and cammingly and slidably received in cam member slot 22b. Link 24 includes a crank portion 24c to accommodate the lateral displacement of the cam plate relative to the pedal arm.

Cable 46 is drivingly secured to one end of the output shaft 66a of a small electric motor 66 (FIG. 3) secured to the dash panel 14 of the vehicle between brake pedal assembly 10 and accelerator pedal assembly 12.

Figures 3, 12, 17, 18:
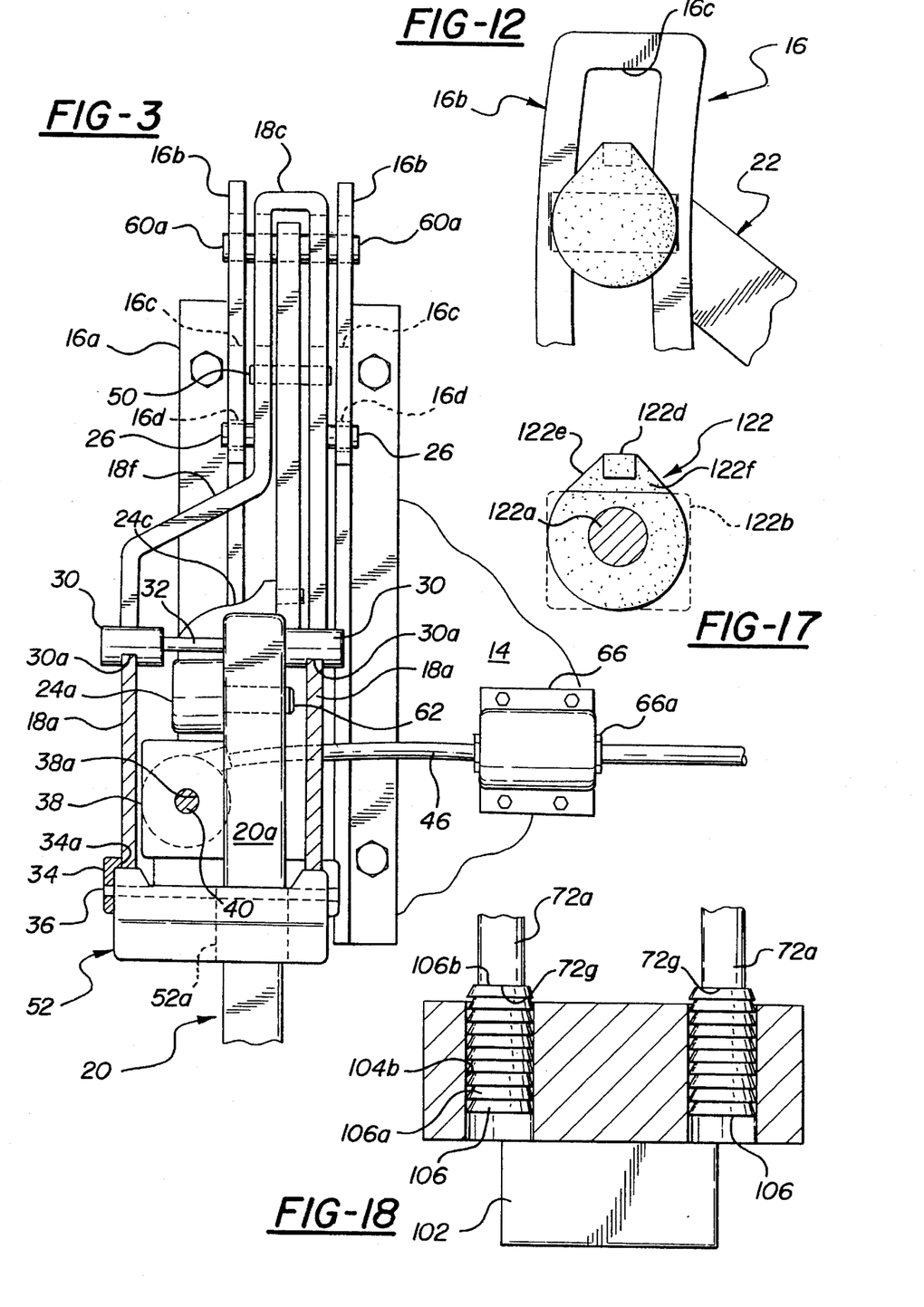

It will be seen that energization of motor 66 results in rotation of cable 46. The rotation of cable 46 is converted by transmission device 42 into rotary movement of screw 40 which in turn coacts with nut 38 to produce linear or sliding movement of pedal arm 20 along adjuster member 18 to selectively adjust the position of pedal pad 28 relative to the driver. As the pedal arm moves fore and aft relative to the adjuster member 18, the link 24 is moved fore and aft to move cam pin 64 in cam plate slot 22b so as to selectively pivot the cam plate about the axis of pin 50 and selectively move pivot axis pin 60 upwardly and downwardly in aligned arcuate slots 18e, 16c so as to selectively adjust the pivot axis of the pedal arm and the adjuster member as the position of the pedal arm is adjusted relative to the adjuster member.

The various parameters of the apparatus are preferably chosen such that the movement of the pivot axis in response to adjusting movement of the pedal arm on the adjuster member has the effect of maintaining a substantially constant ratio between the distance from the pivot axis to the pedal pad and the distance from the pivot axis to the attachment point of the brake actuation rod 48 so as to maintain a substantially uniform mechanical advantage and resultant feel for the brake pedal assembly irrespective of the adjusted position of the pedal arm relative to the adjuster member.

Accelerator pedal assembly 12 (FIG. 1) includes a bracket 70, an adjuster member 72, a pedal arm 74, and a cam member 76. All of the members, unless otherwise indicated, are formed of a suitable ferrous material.

Bracket 70 includes a base portion 70a secured to the dash panel 14 in laterally spaced relation to the brake pedal assembly and a pair of side plate portions 70b extending rearwardly from base portion 70a in laterally spaced relation.

Adjuster member 72 (FIG. 6) includes spaced side plate portions 72a joined at a rearward end wall 72b. One of the side plate portions 72a includes a forward upwardly extending portion 72c defining an attachment flange portion 72d at its upper end for attachment of the accelerator control cable 78. A guide pin 80 proximate the base of upstanding portion 72c guides in an arcuate guide groove 70c in one of the base side plate portions 70b. Each of the side plate portions 72a defines an arcuate generally vertically extending groove 72e proximate its forward end which is vertically aligned with, and corresponding in configuration to, an arcuate groove 70d in the associated bracket side plate portion 70b.

Pedal arm 74 (FIG. 10) has a hollow rearwardly opening U-shaped configuration in cross section and includes an upper portion 74a positioned between adjuster member side plate portions 72a and a lower portion 74b defining a lower end 74c (FIG. 6) for pivotal or fixed attachment of an accelerator pedal 82. A pair of upper guide blocks 84 are pivotally positioned on opposite sides of the upper portion 74a of the pedal arm by a pin 86 passing through the pedal arm and a pair of lower guide blocks 88 are pivotally positioned on opposite sides of the upper portion 74a of the pedal arm by a pin 90 passing through the pedal block. Each upper guide block 84 defines a downwardly opening U-shaped groove 84a slidably engaging the upper edge 72f (FIG. 6) of a respective adjuster member side plate portion 72a and each lower block 88 defines an upwardly opening U-shaped groove 88a slidably engaging the lower edge 72g (FIG. 6) of a respective adjuster member side plate portion 72a. Upper and lower guide blocks 84 and 88 will be seen to mount the pedal arm for selective sliding fore and aft movement along the adjuster member 72 to adjust the position of the accelerator pedal 82 relative to the driver.

A plastic nut 92 (FIGS. 9 and 10) is fixedly positioned between the spaced side walls 74d of the upper end of the pedal arm and includes a threaded bore 92a threadably receiving a screw member 94 secured to the output shaft of a transmission device 96 (FIG. 6) suitably secured to one of the side plate portions 72a of the adjuster member and including a cable input fitting 96a receiving a cable 98 connected to the other end of the output shaft 66a of electric motor 66 (FIG. 3). Transmission device 96 may be identical to the transmission device 42 of the brake pedal assembly. It will be seen that energization of motor 66 provides rotary cable movement to the accelerator assembly 12 which is converted to rotary movement of screw member 94 by transmission device 96 so as to move the pedal arm fore and aft slidably along the adjuster member to selectively adjust the position of accelerator pedal 82 relative to the driver.

A slack takeup device 100 (FIGS. 6, 7, 8 and 18) is positioned at the intersection of the upper end 74a of the pedal arm and the adjuster member. Slack takeup device 100 includes a bracket 102 secured as by welding to the rear face 74e of the pedal arm immediately below the intersection of the pedal arm and the adjuster member, and a plastic block 104 including a groove 104a receiving the rearward end portion 102a of bracket 102 so as to position the block 104 in underlying relation to the adjacent portion of the adjuster member. Takeup assembly 100 further includes a pair of plugs 106 received in a pair of vertical bores 104b in block 104 and including ratchet teeth 106a. Plugs 106 may, for example, be of the type available from Penn Engineering and Manufacturing Company of Danboro, Pa. as Part No. NPPA-M5. Following the assembly of the pedal arm to the adjuster member to mount the pedal arm slidably on the adjuster member, plugs 106 are inserted upwardly through bores 106a until the upper ends 106b of the plugs engage the lower edges 72g of the side arm portions 72a of the adjuster member so as to take up slack in the pedal arm and adjuster member at the intersection of the pedal arm and adjuster member and preclude inadvertent angular movement between the pedal arm and the adjuster member so as to eliminate rattle in the pedal assembly and provide a firm solid feel for the driver's foot against the accelerator pedal 82. The plugs 106 will be understood to rigidly maintain the position to which they are moved to take up the slack by virtue of the sliding engagement of the ratchet teeth 106*a* with the adjacent plastic material of the bores 104*b* of the block.

Cam member 76 (FIGS. 6 and 10) includes a pivot portion 76*a* passing a pivot pin 108 extending between guide member side plate portions 72*a* so as to pivotally mount the cam plate on the adjuster member; a forward portion 76*b* mounting a pivot axis pin 110 including laterally extending portions 110*a* respectively slidably mounted in aligned slots 70*d*, 72*e* of the adjuster member and bracket; and a lower portion 76*c* defining an arcuate slot 76*d*. Lower cam plate portion 76*c* is positioned between the spaced side walls 74*d* of the pedal arm with a cam pivot pin 112 mounted in the pedal arm side plate portions 74*d* passing through the slot 76*d* for camming coaction with the slot. Spacers 114 maintain the lower portion 76*c* of the cam member in a central position between the side walls 74*d* of the pedal arm.

Figures 5, 6, 7, 8:
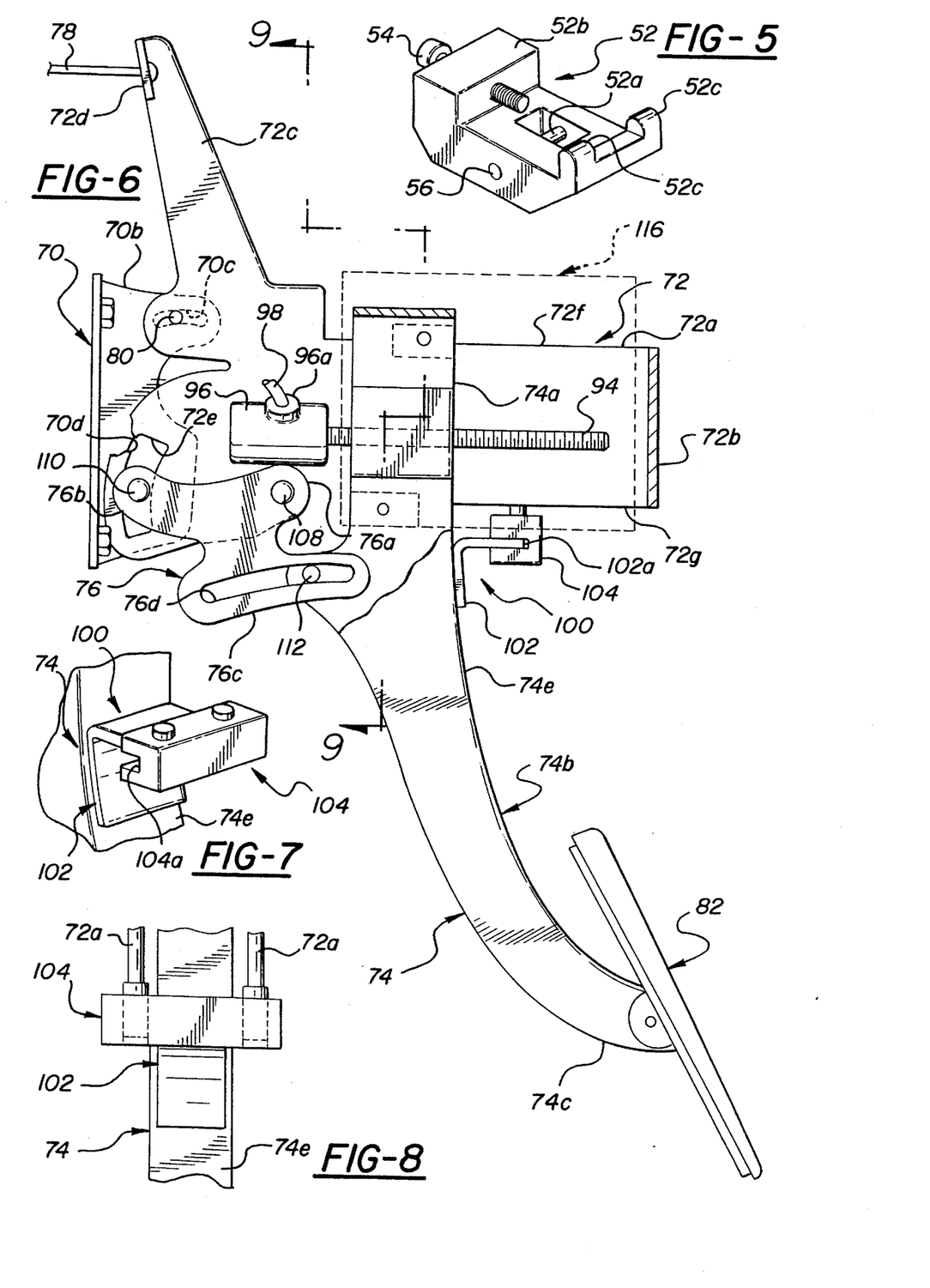
FIG. 5 is a detail view of an element of the brake control pedal assembly.
FIG. 6 is a somewhat schematic view of the accelerator control pedal assembly.
FIGS. 7 and 8 are detail views of the accelerator control pedal assembly.
Figures 9, 10, 11:
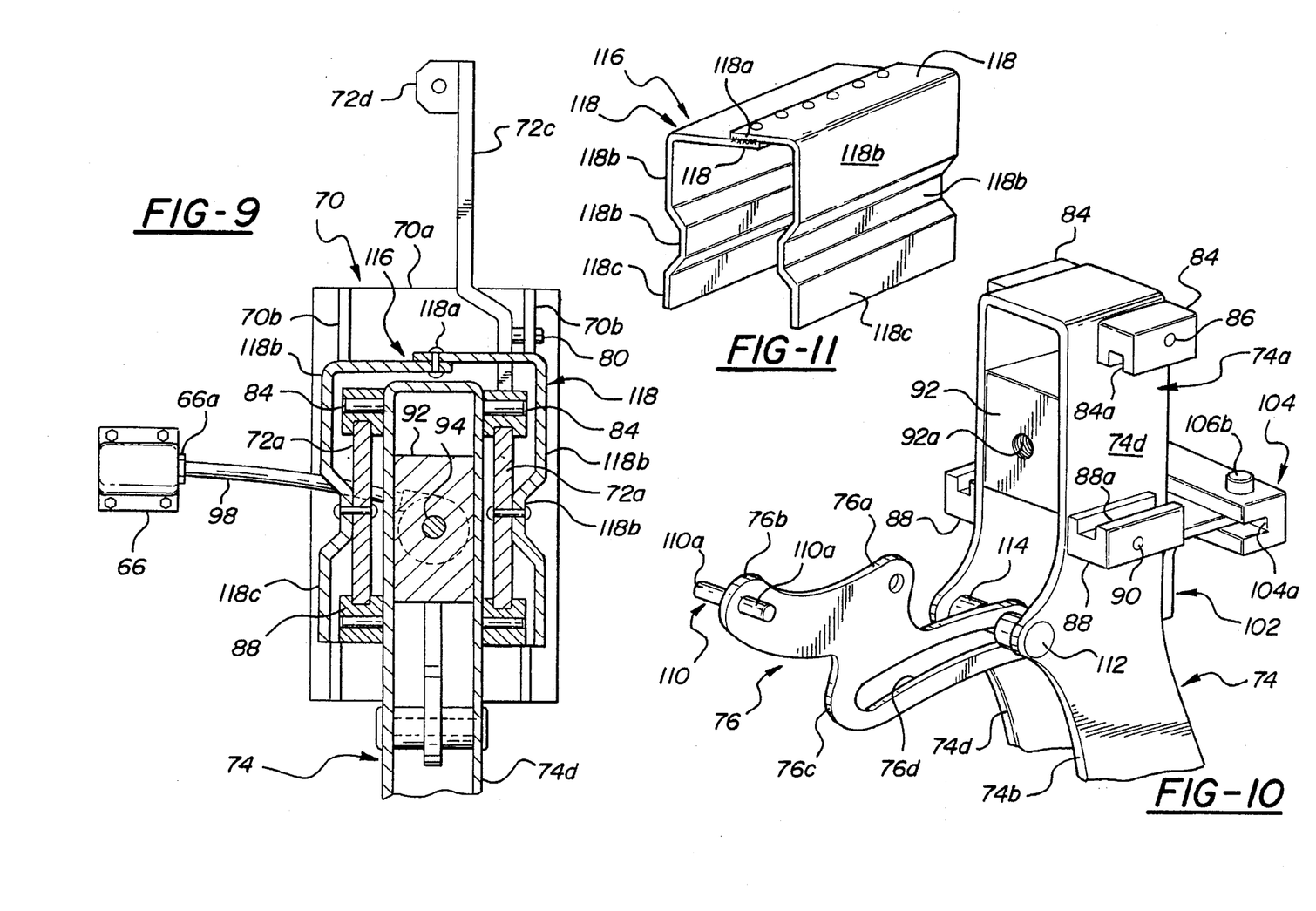
FIG. 9 is a cross-sectional view taken on line 9—9 of FIG. 6.
FIG. 10 is a fragmentary perspective view of a portion of the accelerator pedal assembly.
FIG. 11 is a perspective view of an element of the accelerator pedal assembly.
Figure 14:
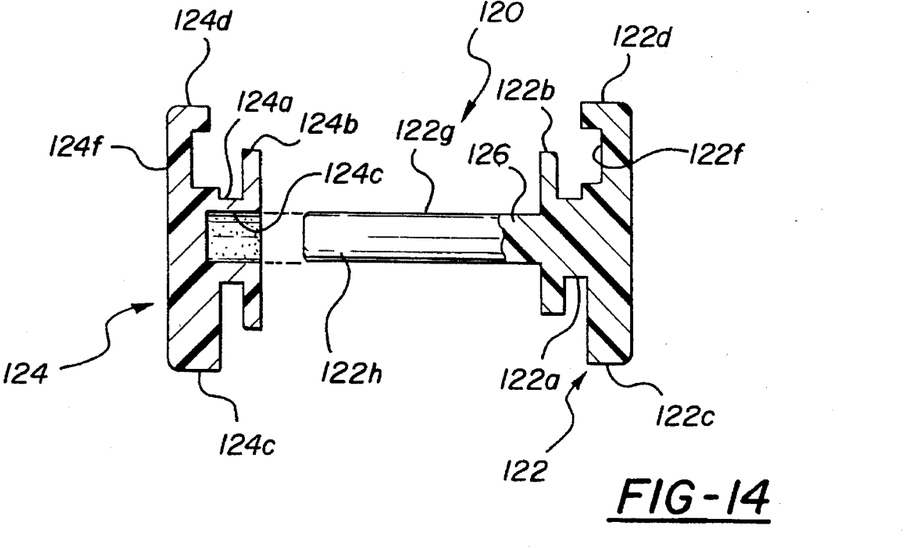
Figures 15, 16:
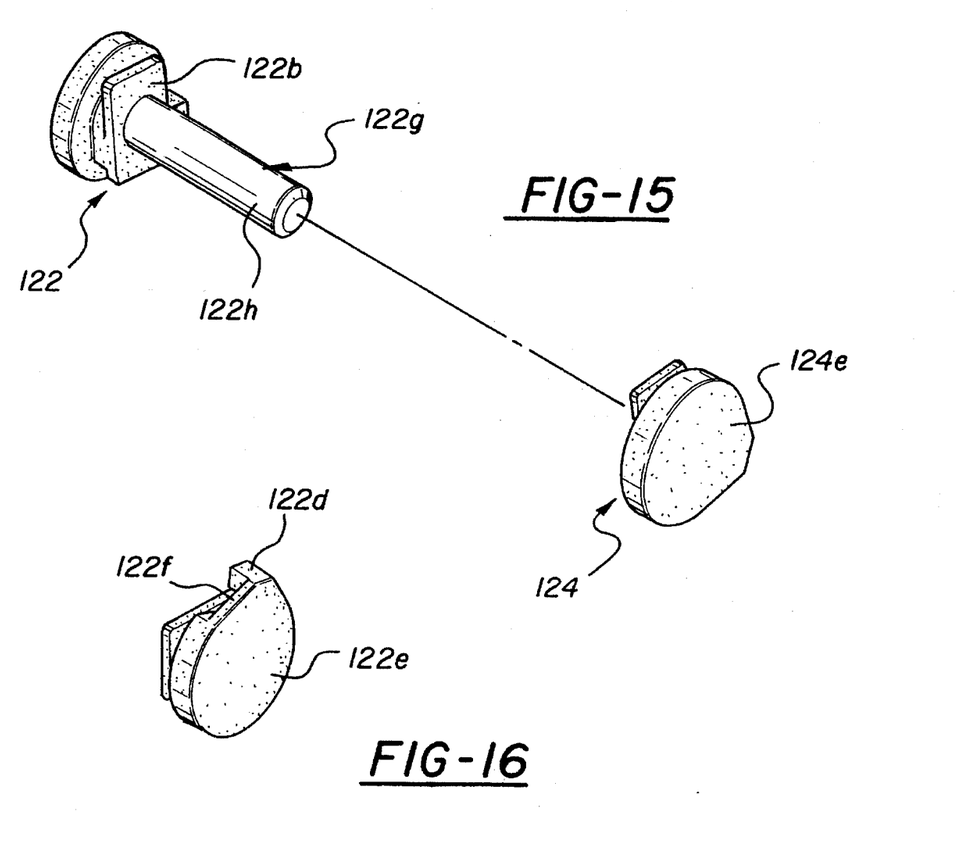

In the operation of the invention accelerator pedal assembly, upon energization of motor 66, cable 98 is rotated to deliver a rotary cable movement to the accelerator pedal assembly which is converted to rotary movement of screw member 94 by transmission device 96. As screw member 94 is rotated, the screw member coacts with nut 92 to move the pedal arm selectively fore and aft along the adjuster member to selectively adjust the position of the accelerator pedal 82 relative to the driver. As the pedal arm moves fore and aft relative to the adjuster member, cam pin 112 rides in cam member slot 76*d* to pivot the cam plate 76 about the axis of pin 108 and selectively adjust the position of pivot axis pin 110 in slots 72*e* and 70*d* so as to selectively adjust the position of the pivot axis of the pedal arm and the adjuster member. The parameters of the various elements are selected such that a substantially fixed ratio is maintained between the distance from the pivot axis 110 to the pedal pad 82 and the distance from the pivot axis 110 to the attachment point of the accelerator cable 78 irrespective of the position of adjustment of the pedal arm on the adjuster member so as to maintain a substantially constant mechanical advantage and feel for the accelerator pedal irrespective of the position of the pedal arm.

The accelerator pedal assembly 12 further includes a cover assembly 116 (FIGS. 9 and 11) of inverted U configuration. Cover assembly 116 is formed from a pair of cover members 118 secured together as by riveting or other means along their upper edges 118*a* in overlying relation to the adjuster member. Each cover member 118 further includes a skirt portion 118*b* extending downwardly in spaced relation along a respective side face of the adjuster member and including an inturned portion 118*b* riveted or otherwise fixedly attached to the respective outboard face of an adjuster member side plate portion 72*a*. Each cover member 118 terminates in a lower portion 118*c* extending downwardly to a location proximate the lower faces of lower guide blocks 88. Cover assembly 116 will be seen to fit over and straddle the adjuster member side plate portions 70*a* and the guide blocks 84,88 so as to protect the sliding interface between the pedal arm and the adjuster member against abrasives, contaminants and the like. Cover assembly 116 further, by virtue of the structural connection to the side plate portions 72*a* of the adjuster member, serves to substantially rigidify the adjuster member so as to fixedly maintain the lateral spacing between side plate portions 72*a* and thereby facilitate the sliding movement of the pedal arm along the adjuster member.

The bushing assembly 120 seen in FIGS. 12–17 is suitable for use with either the brake control pedal assembly of the invention or the accelerator control pedal assembly of the invention but is illustrated in the FIGURES in association with the brake pedal assembly. The bushing assembly is intended to provide a ready and convenient means of providing and maintaining the proper spacing between the respective bracket portion 16*b* and adjuster member portions 18*d* so as to positively mount the cam member rearward portion 22*c* on the pivot axis and preclude undesired lateral migration of the cam member during operation of the adjuster mechanism.

Bushing assembly 120 includes a first bushing member 122 and a second bushing member 124 which coact in their assembled relation to maintain the bracket and adjuster member portions 16*b*/18*d* in positive spaced relation and define the pivot axis for the cam member 22.

First bushing member 122 includes a central portion 122*a* of circular cross section defining a central axis 126 and having a diameter approximating the transverse width of the slot 16*c* in bracket portion 16*b*; an inboard portion 122*b*, connected to the inboard end of central portion 122*a*, of generally rectangular configuration and having a major diametric dimension exceeding the width of slot 16*c* and a minor diametric dimension less than the width of slot 16*c*; an outboard portion 122*c* of generally circular configuration and having a diametric dimension exceeding the width of slot 16*c* and including an axially inwardly extending locking tab portion 122*d*. Locking tab portion 122*d* is formed on an eccentric portion 122*e* of the outboard portion, is sized to fit loosely in slot 16*c*, and is joined to the main body of outboard portion 122*c* by a thin web portion 122*f* so as to mount the locking tab portion 122 for flexing movement in an axial direction relative to the main body of the outboard portion.

First bushing member 122 further includes a pivot shaft portion 122*g* extending axially inboard from inboard portion 122*b* along central axis 126. Pivot shaft portion 122*g* has a circular configuration and has a diameter approximating the width of the slot 18*e* in adjuster member portions 18*d*.

Second bushing member 124 includes a central portion 124*a* of circular cross section having a diameter approximating the transverse width of slots 16*c*; an inboard portion 124*b*, connected to the inboard end of central portion 124*a*, of generally rectangular configuration and having a major diametric dimension exceeding the width of slot 16*c* and a minor diametric dimension less than the width of slot 16*c*; and an outboard portion 124*c* having an generally circular configuration and having a diametric dimension exceeding the width of slot 16*c* and including an axially inwardly extending locking tab portion 124*d* positioned radially outwardly of central portion 124*a*. Locking tab portion 124*d* is provided on an eccentric portion 124*e* of outboard portion 124*c* and is connected to the main body of outboard portion 124*c* by a thin web portion 124*f* so as to allow the locking tab to flex axially relative to the main body of the outboard portion.

First bushing member 122 is passed through the slots 16*c*, 18*e* of the righthand adjuster member and bracket portions (as viewed in FIG. 13) inboard end first with the major dimension of the inboard end portion 122*b* in longitudinal alignment with the slot 16*c* to position the inboard end portion inboard of the slot 16c, position the central portion 122a in the slot 16c, position the outboard end portion 122d outboard of the slot 16c, and position the locking tab portion 122d resiliently against the outboard face of the bracket portion 16b transversely of the slot 16c, whereafter the bushing member 120 may be rotated about the axis 126 to position the major dimension of the inboard portion 122b transversely of the slot 16c to preclude withdrawal of the bushing member from the slot and move locking tab portion 122d snappingly into the slot 16c to preclude return rotation of the bushing member. Pivot shaft portion 122g extends through slot 18e in righthand adjuster member 18d, through an aperture in cam member 22, and through the slot 18e in the lefthand adjuster member 18d.

Second bushing member 124 is passed through the slot 16c in the lefthand bracket portion 16b (as viewed in FIG. 13) inboard end portion first with the major dimension of the inboard end portion 124b in longitudinal alignment with the slot 166 to position the inboard end portion inboard of the slot 16c, position the central portion 124a in the slot, position the outboard end portion 124c outboard of the slot, and position the locking tab portion 124d resiliently against the outboard face of the lefthand bracket portion 16b transversely of the slot 16c, whereafter the bushing member may be rotated about axis 126 to position the major dimension of the inboard portion 124 transversely of the slot 16c to preclude withdrawal of the bushing member from the slot and move locking tab portion 124b snappingly into the slot 16c to preclude return rotation of the bushing member. As the bushing member 124 is moved inboard through slot 16c an inboard bore 124g passes over the free end 122h of pivot shaft portion 122g of bushing member 122 to telescopically arrange the first and second bushing members.

In their installed and rotated positions, inboard portion 124b of second bushing member 124 serves as a spacer between the lefthand bracket portion 16b and the lefthand adjuster member portion 18d and inboard portion 122b of first bushing member 122 serves as a spacer between the righthand bracket portion 16b and the righthand adjuster member portion 18d so that the assembled bushing members 122 and 124 coact to positively and precisely space the left and right bracket portions and adjuster member portions, and pivot shaft portion 122g of first bushing member 122 defines the pivot shaft to receive and pivot cam member 22. Further washers or bushings 130 are positioned on opposite side faces of the cam member 22 on pivot shaft portion 122g to space the cam member 22 from the respective adjuster member portions 18d. The bushing assembly 120 will be seen to provide a ready and easily installed means of properly spacing the bracket portions and the adjuster member portions to preclude undesired lateral migration of the cam member during operation of the apparatus.

Whereas preferred embodiments of the invention have been illustrated and described in detail, it will be apparent that various changes may be made in the disclosed embodiments without departing from the scope or spirit of the invention.

We claim:

1. An adjustable control pedal apparatus for a motor vehicle comprising an adjuster member defining a mounting portion and a pedal arm member defining a mounting portion mounted for sliding movement along said adjuster member mounting portion and defining an intersection with said adjuster member portion, characterized in that the apparatus further includes a slack takeup assembly positioned at said intersection and operative to preclude relative angular movement between said members at said intersection, said slack takeup assembly including a block positioned at said intersection and a plurality of plug members mounted in said block and extending beyond said block to engage a face of said adjuster member portion.

2. An apparatus according to claim 1 wherein said block includes a plurality of generally vertical through bores and said plugs are inserted upwardly into said bores to press the upper ends of the plugs against the face of the adjuster member portion.

3. An adjustable control pedal apparatus for a motor vehicle comprising an adjuster member defining a mounting portion and a pedal arm member defining a mounting portion mounted for sliding movement along said adjuster member mounting portion and defining an intersection with said adjuster member portion, characterized in that the apparatus further includes a slack takeup assembly positioned at said intersection and operative to preclude relative angular movement between said members at said intersection, said slack takeup assembly including a lever pivotally mounted on said pedal arm member portion proximate said intersection and including a portion engaging an adjacent face of said adjuster member portion, and means operative to maintain said lever portion in contact with said adjuster member portion face.

4. An apparatus according to claim 3 wherein said means comprises a screw passing through a threaded bore in said lever and including a free end engaging a face of said pedal arm member portion.

5. An adjustable control pedal apparatus for a motor vehicle comprising an adjuster member, a pedal arm mounted for sliding movement on said adjuster member, and means operative in response to sliding movement of the pedal arm on the adjuster member to adjust the pivot axis of the control pedal apparatus, characterized in that said means includes a cam member, a pivot axis pin mounted on said cam member and defining the pivot axis of the control pedal apparatus, and an elongated link extending in the direction of sliding movement of the pedal arm, pivotally connected at one end to said pedal arm, and cammingly coacting at its other end with said cam member.

6. An adjustable control pedal apparatus for motor vehicle comprising:

a generally horizontally extending adjuster member;

a generally vertically extending pedal arm slidably mounted on the adjuster member and extending downwardly from the adjuster member;

a cam member pivoted on the adjuster member and including a slot totally bounded by said cam member and a pivot axis pin defining the pivot axis of the adjuster member and pedal arm; and     a cam pin mounted on said pedal arm beneath the adjuster member, received in said slot, and operative in response to sliding movement of said pedal arm on said adjuster member to pivot said cam member on said adjuster member and adjust the position of said pivot axis pin and thereby of said pivot of the adjuster member and pedal arm.

7. An adjustable control pedal apparatus for a motor vehicle comprising an adjuster member, a pedal arm mounted for sliding movement on said adjuster member, and means operative in response to sliding movement of the pedal arm on the adjuster member to adjust the pivot axis of the control pedal apparatus, characterized in that said means includes a cam member, a pivot axis pin mounted on said cam member and defining the pivot axis of the control pedal apparatus, and a link connected at one end to said pedal arm and cammingly coacting at its other end with said cam member, said cam member being pivotally mounted on the adjuster member, said one end of said link being pivotally mounted on said pedal arm, said other end of said link being received in a slot in said cam member, and said pivot axis pin being received in a slot in said adjuster member.

8. An adjustable control pedal apparatus for a motor vehicle comprising:

an adjuster member;

a pedal arm slidably mounted on the adjuster member;

a cam member pivoted on the adjuster member and including a slot and a pivot axis pin defining the pivot axis of the adjuster member and pedal arm;

a cam pin received in said slot and operative in response to sliding movement of said pedal arm on said adjuster member to pivot said cam member on said adjuster member and adjust the position of said pivot axis pin and thereby of said pivot axis of the adjuster member and pedal arm; and a link pivotally mounted at one end on said pedal arm, said cam pin being mounted on the other end of said link.

9. An adjustable control pedal apparatus for a motor vehicle comprising:

an adjuster member adapted to be pivotally mounted relative to the vehicle body structure and defining a pair of laterally spaced elongated generally horizontally extending side plates;

a pedal arm including a lower portion mounting a control pedal and an upper portion positioned between said adjuster member side plates and defining laterally spaced generally vertically extending side walls extending downwardly from said adjuster member;

a nut positioned between said laterally spaced side walls and including a threaded bore for threaded coaction with a screw drive member;

an upper pair of guide blocks positioned on opposite sides of said pedal arm upper portion and respectively slidably engaging the upper edges of said adjuster member side plates;

a lower pair of guide blocks positioned on opposite sides of said pedal arm upper portion and respectively slidably engaging the lower edges of said adjuster member side plates;

a cam member carrying a pivot axis pin defining a pivot axis of the apparatus and defining a cam slot; and a cam pin extending between the side walls of the pedal arm beneath the nut and positioned slidably in said slot.

10. An adjustable control pedal apparatus for a motor vehicle comprising:

an adjuster member adapted to be pivotally mounted relative to the vehicle body structure and defining a pair of laterally spaced elongated side plates;

a pedal arm including a lower portion mounting a control pedal and an upper portion positioned between said adjuster member side plates and defining laterally spaced side walls;

a nut positioned between said laterally spaced side walls and including a threaded bore for threaded coaction with a screw drive member;

an upper pair of guide blocks positioned on opposite sides of said pedal arm upper portion and respectively slidably engaging the upper edges of said adjuster member side plates;

a lower pair of guide blocks positioned on opposite sides of said pedal arm upper portion and respectively slidably engaging the lower edges of said adjuster member side plates; and a cover of inverted U-configuration fitted over and straddling said adjuster member side plates, whereby to protect the sliding interface of said guide blocks and said side plates, and including portions fixedly secured to the respective outboard faces of said side plates, whereby to rigidify said adjuster member.

* * * * *

UNITED STATES PATENT AND TRADEMARK OFFICE
CERTIFICATE OF CORRECTION

PATENT NO. : 5,460,061
DATED : October 24, 1995
INVENTOR(S) : Harry Redding, Christopher Bortolon It is certified that error appears in the above-indentified patent and that said Letters Patent is hereby corrected as shown below:

Column 3, Line 39, insert paragraph --FIG. 18 is a detailed view of the accelerator control pedal assembly.--

Column 5, Line 3, delete "52b" and insert --52c--.

Column 5, Line 16, "(FIG.3)" should be before "extending" not before "including".

Column 9, Line 19, delete "166" and insert --16C--.

Signed and Sealed this

Seventh Day of May, 1996

Attest:

BRUCE LEHMAN

Attesting Officer

Commissioner of Patents and Trademarks